(12) United States Patent
Fischer et al.

(10) Patent No.: US 6,468,080 B1
(45) Date of Patent: Oct. 22, 2002

(54) DENTAL WEDGE INCORPORATING MECHANICALLY FLEXIBLE FEATURES

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/946,122

(22) Filed: Sep. 4, 2001

(51) Int. Cl.[7] .................................................. A61C 7/00
(52) U.S. Cl. ...................................................... 433/149
(58) Field of Search .......................................... 433/149

(56) References Cited

U.S. PATENT DOCUMENTS

| | | |
|---|---|---|
| 109,665 A | 11/1870 | Richards |
| 350,150 A | 10/1886 | Parr ........................... 433/149 |
| 421,925 A | 2/1890 | Graves |
| 523,136 A | 7/1894 | Trakofler |
| 1,529,075 A | 3/1925 | McIntyre |
| 1,657,497 A | 1/1928 | Cichon |
| 2,083,131 A | 6/1937 | Tornebohm .................. 206/16 |
| 2,150,005 A | 3/1939 | McNinch ..................... 433/149 |
| 3,193,094 A | 7/1965 | Schulstad .................... 433/149 |
| 3,473,226 A | 10/1969 | Arlers et al. ................. 433/149 |
| 3,510,948 A | 5/1970 | Walthall ....................... 433/149 |
| 3,636,631 A | 1/1972 | Tofflemire ...................... 32/64 |
| 3,815,243 A | 6/1974 | Eames ......................... 433/149 |
| 3,890,714 A * | 6/1975 | Gores .......................... 433/149 |
| 4,337,041 A | 6/1982 | Harsany ....................... 433/149 |
| 4,449,933 A * | 5/1984 | Forni ........................... 433/149 |
| 4,696,646 A | 9/1987 | Maitland ...................... 433/149 |
| 4,878,508 A | 11/1989 | Durbin ......................... 132/329 |
| 5,230,263 A | 7/1993 | Kwaka ......................... 81/125.1 |
| 5,448,932 A | 9/1995 | Zurbuchen et al. ......... 81/124.4 |
| 5,836,767 A | 11/1998 | Aspel ........................... 433/229 |
| 5,890,900 A | 4/1999 | Fischer et al. .............. 433/149 |
| 5,890,901 A | 4/1999 | Fischer et al. .............. 433/149 |
| 6,074,210 A * | 6/2000 | Garrison ...................... 433/149 |
| 6,142,781 A | 11/2000 | Fischer ........................ 433/149 |
| 6,220,858 B1 * | 4/2001 | McKenna et al. ........... 433/149 |
| 6,234,793 B1 | 5/2001 | Brattesamo et al. .......... 433/39 |

* cited by examiner

Primary Examiner—Cary E. O'Connor
(74) Attorney, Agent, or Firm—Workman, Nydegger & Seeley

(57) ABSTRACT

The invention generally provides for a dental wedge with flexible members. The dental wedge comprises a wedge shaped body with sides that are serrated with multiple flexible members extending away from the sides. When the dental wedge is inserted between adjacent teeth, the flexible members bend and conform to the surfaces of the teeth. This generally increases the frictional surface area between the dental wedge and the teeth, thereby providing the dental wedge with increased retention capabilities for remaining in place between the teeth. In some embodiments, the flexible members also comprise edges and/or gritty surfaces for further increasing the retention capabilities of the dental wedge.

20 Claims, 3 Drawing Sheets

DENTAL WEDGE INCORPORATING MECHANICALLY FLEXIBLE FEATURES

BACKGROUND OF THE INVENTION

1. The Field of the Invention

The present invention is in the field of dental retention devices. In particular, the present invention relates to dental wedges that are used for separating teeth and for holding matrix bands against teeth during dental procedures. Even more particularly, the present invention relates to dental wedges comprising mechanically flexible features.

2. The Prior State of the Art

In the field of dentistry, dental practitioners often treat patients who have developed cavities in teeth. In order to treat cavities the dental practitioner removes the infected portion of the tooth and then deposits a filling material such as a composite, a resinous material, or an amalgam into the tooth preparation.

During the dental filling procedure, a matrix band is typically placed against the side of the tooth to keep the filling material within the tooth preparation from flowing beyond the desired boundary of the restored tooth. A matrix band typically comprises a thin metallic or plastic strip that is flexible and can be bent around the tooth being restored. If the matrix band is not properly held in place then the filling may be expressed beyond the tooth preparation, thereby distorting the configuration of the restored tooth and possibly causing ledges or overhangs, which can be problematic to adjacent tissues and inhibit cleaning.

An improper filling can lead to dental discomfort, misalignment of teeth, capture of food particles, infections, and other dental problems. To avoid these problems, and to fix a distorted dental filling, it may be necessary to grind or drill the filling material down to the proper shape, or even replace the filling entirely. It is desirable to avoid this process because it can increase the time and expense of restoring the tooth and can also create anxiety and discomfort to the patient being treated. Accordingly, it is desirable to keep the matrix band in proper placement during the filling procedure so that the dental filling material molds into a shape that approximates the desired shape of the restored tooth and fits precisely.

In order to hold the matrix band in a desired placement, small dental wedges are often placed into the interproximal spaces between the matrix band and the adjacent tooth. Sometimes, dental wedges are also used to separate the teeth to make room to accommodate, or to compensate for, the thickness of the matrix band between the teeth. Existing dental wedges are typically composed of a wood or semi-rigid plastic material having properties that enable the dental wedge to be slightly deformed while maintaining a sufficiently rigid or semi-rigid structure. These properties generally enable the dental wedge to force teeth apart without damaging the teeth. After the dental wedge is removed the compressed periodontal fibers return to their original dimension and cause the displaced teeth to return to their designated positions.

One inherent problem with the use of dental wedges, however, is that they are prone to slipping out from between the teeth during the dental procedure because the frictional forces holding the dental wedges in place are not adequate. Additionally, existing dental wedges are particularly susceptible to slipping out of place because they are generally incapable of conforming to and accommodating the irregularities of, and between, the teeth. They therefore make only limited contact- with the teeth, thereby further limiting the frictional forces necessary to hold the dental wedges in place. This is particularly problematic when the surfaces of the dental wedges become wet and slippery from the patient's saliva or blood, thereby further decreasing the friction that is applied over this limited area of contact between the dental wedges and the surfaces of the teeth.

One attempt to address the problems associates with rigid wedges is the FLEXI-WEDGE, which is made from a semi-rigid plastic material and which has a generally upside-down V-shaped cross section. This makes it capable of flexing along its base as it is forced between teeth. Nevertheless, the FLEXI-WEDGE also suffers from an inability to accommodate and conform to irregularities of, and between, the teeth.

Accordingly, there is currently a need in the art for an improved dental wedge with improved retention capabilities for remaining in place within the interproximal space between teeth, for spacing teeth apart, and for holding matrix bands in proper placement during dental procedures.

SUMMARY OF THE INVENTION

The present invention is directed to improved dental wedges for use in dental procedures. In particular, dental wedges of the invention have protruding flexible members that help the dental wedges stay in place when inserted between adjacent teeth.

In one presently preferred embodiment, a dental wedge of the invention comprises a rigid body that is substantially wedge shaped, tapering from a head to a tip and comprises multiple flexible members that protrude away from the sides of the dental wedge. Said in another way, the sides of the dental wedge are serrated, with multiple tines or teeth protruding away from the sides of the dental wedge. According to one presently preferred embodiment, these protrusions or members that protrude away from the sides of the dental wedge are somewhat flexible and are configured to bend when they are subjected to an adequate force, such as when being inserted between two adjacent teeth.

It should be appreciated that the shape and size of the flexible members may vary to accommodate different needs and preferences. For instance, the flexible members may be rounded, pointed, curved, rectilinear, triangular, straight, thin, thick, textured, smooth, or any combination thereof.

In one preferred embodiment, the body of the dental wedge and the flexible members comprise an integrated unit that is manufactured during a single process, such as by injection molding or casting. According to this embodiment, the body of the dental wedge and the flexible members may be composed of a semi-rigid material, such as nylon, polycarbonate, polystyrene, polyethylene, and polypropylene. It should be appreciated, however, that the dental wedges of the invention may also comprise other suitable materials, including, but not limited to various thermoplastics, thermoset plastics, and chemical set plastics.

According to one alternative embodiment, the flexible members are formed separately from the body and are subsequently attached to the body, such as with ultrasonic welding, friction welding, or insert molding. The flexible members may also be attached to the body with an adhesive, such as with glue, epoxy, or cement. The flexible members may be composed of the same material as the body or of a different material.

In one preferred embodiment, when a dental wedge of the invention is inserted between adjacent teeth, the flexible members are forced to bend between the teeth and the body of the dental wedge, thereby enabling the flexible members to conform to the surfaces of the teeth. By conforming to the shape of the teeth, the flexible members are able to increase the surface area over which friction is applied to the dental wedge, thereby helping hold the dental wedge in place and keeping the dental wedge from slipping out from between the teeth. To further enhance the retention capabilities of the dental wedges of the invention, the flexible members may also be configured with sharp edges or gritty surfaces that can catch onto irregularities of the tooth surface, thereby increasing the frictional forces applied by the dental wedge.

The dental wedges of the invention can also be used to securely hold a matrix band conformingly in place against a tooth. For instance, when a dental wedge of the invention is placed next to a matrix band between adjacent teeth, the flexible members of the dental wedge apply multiple discrete forces to the matrix band urging the matrix band to conform to the shape of the tooth.

These, as well as other, benefits, features and advantages of the dental wedges of the present invention will become more fully apparent from the following description and appended claims, or may be learned by practicing the invention as set forth below.

BRIEF DESCRIPTION OF THE DRAWINGS

A more extensive description of the present invention, including the above-recited features and advantages, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which.

DETAILED DESCRIPTION OF THE PREFERRED EMBODIMENTS

The present invention relates to improved dental wedges, and more particularly, to dental wedges having protruding flexible members that provide improved retention capabilities for keeping the dental wedges in place within the interproximal spaces between adjacent teeth.

Typically, when teeth are separated with a dental wedge, periodontal fibers attached to the teeth apply a countervailing force that pulls the teeth back together. This force is transferred from the teeth to the dental wedge and tends to urge the dental wedge out from between the teeth. This is an inherent problem with existing dental wedges of the prior art, in that they are susceptible to slipping out from between the teeth.

The dental wedges of the present invention overcome this problem by providing flexible members that are generally able to conform to the irregularities and contours of the teeth, thereby increasing the frictional forces and retention capabilities of the dental wedge for enabling the dental wedges of the invention to remain in place within the interproximal spaces between the teeth. The flexible members may comprise various shapes, which shapes, as described herein, generally refer to the two-dimensional footprints of the flexible members. It should be appreciated, however, that the shapes of the flexible members may also vary three-dimensionally.

Figure 1:
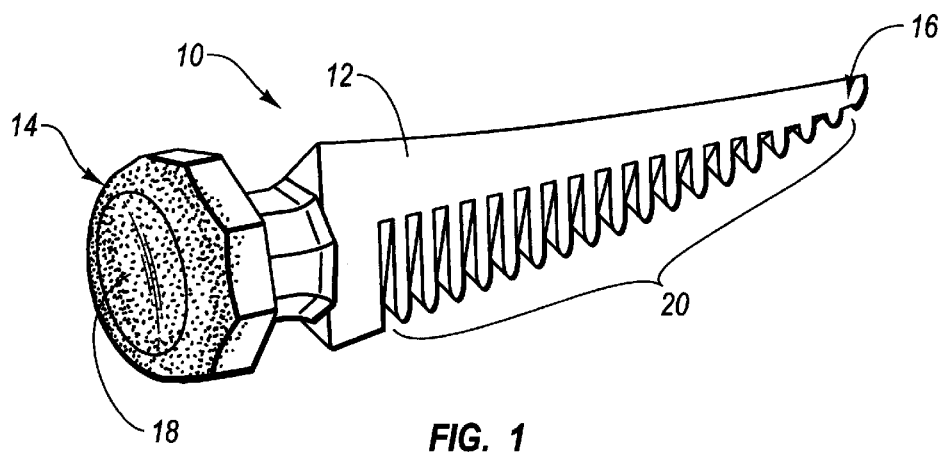
FIG. 1 is a perspective view of one embodiment of the dental wedge of the present invention that includes a head, a serrated body with multiple flexible members, and a tip.

FIG. 1 illustrates one presently preferred embodiment of a dental wedge 10 of the invention comprising a body 12, which is substantially rigid, and which extends from a proximal end 14 to a distal end 16. As defined herein, the terms "rigid" and "substantially rigid" are used interchangeably, and refer to the condition of inflexibility, such that the body 12 is not flexible and cannot easily be bent. Although the body 12 may be composed of a semi-rigid material, the thickness and shape of the body 12 causes the body 12 to behave as a substantially rigid object.

According to one preferred embodiment, the shape of the body 12 comprises a substantially triangular cross-sectional area with a top edge, two bottom edges and a base that extends across the two bottom edges. The body 12 also comprises sides that are defined by, and extend between, the top and bottom edges.

As shown, the proximal end 14 of the body 12 may comprise an octagonal shaped head to facilitate gripping of the dental wedge 10 with fingers, cotton pliers or other appropriate instruments. The octagonal shaped head is particularly useful for enabling dental practitioners to insert dental wedge 10 into the interproximal space between adjacent teeth at various angles of orientation, as needed. It should be appreciated, however, that the shape of proximal end 14 may vary and is not limited to the octagonal head shape shown in FIG. 1.

As shown, the proximal end 14 also comprises a face 18 which is preferably textured and concaved. The concaved shape and texture of face 18 is useful for overcoming a common problem with existing dental wedges, in which tools that are used to push the dental wedges into the interproximal spaces between teeth are susceptible to slipping off of the dental wedges while applying a force to the dental wedges. This is a problem because the tool can potentially cause damage to teeth and sensitive mouth tissue when they slip off of the dental wedges. The present embodiment of the invention overcomes this problem by providing a contour and texture that helps to prevent tools from slipping off of the face 18 while applying a force to dental wedge 10.

Other benefits and features of texturing the face and proximal end of a dental wedge are described in U.S. patent application Ser. No. 09/707,183, filed Mar. 19, 2001, and entitled "Dental Wedges Having Proximal Ends With Gritty Top Layers," which is incorporated herein by reference.

Figure 2:
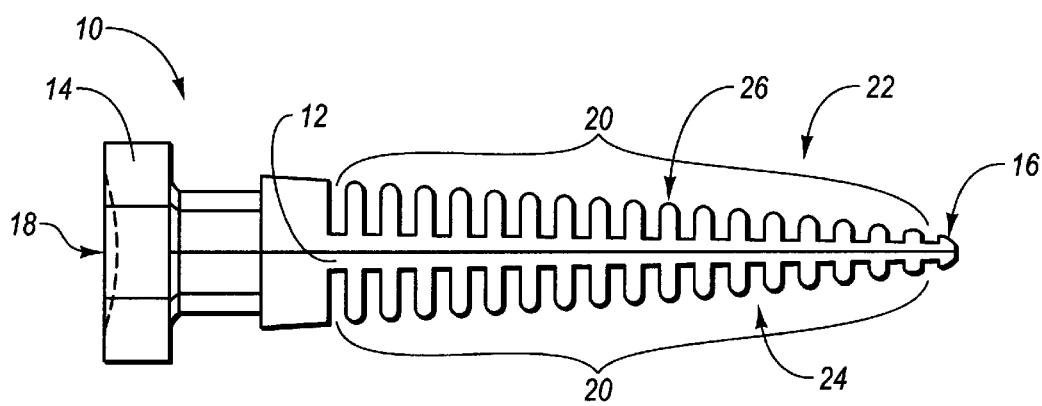
FIG. 2 is a top view of the dental wedge of FIG. 1 that illustrates the multiple flexible members are curved at their ends and that they protruding away from the sides of the body.

As shown in FIG. 1, the dental wedges 10 of the invention also comprise multiple flexible members 20. The flexible members 20 are positioned along and protrude away from the sides 22 and 24 of the dental wedge 10, near the base of the dental wedge 10, and as shown in FIG. 2, generally provide the dental wedge 20 with serrated edges. Although the flexible members 20 are shown to protrude from both sides 22 and 24 of the dental wedge 10, it should be appreciated that the flexible members 20 may be configured on only a single side 22 or 24 or any single portion of the dental wedge 10.

According to one presently preferred embodiment, the flexible members 20 are composed of a semi-rigid material and are configured to bend when they are subjected to the forces that are required to insert the dental wedge 10 between two adjacent teeth. It will be appreciated that the flexibility of flexible members 20 may vary according to the shape and material composition of the flexible members 20, which may vary in different embodiments.

In one preferred embodiment, the body 12 of the dental wedge 10 and the flexible members 20 are manufactured at the same time, such as by injection molding, casting or hot stamping. According to an alternative embodiment, the body 12 of the dental wedge 10 is initially formed and then subsequently machined to remove excessive material from the dental wedge 10 around and between the flexible members 20.

According to yet another embodiment, the body 12 of the dental wedge 10 and the flexible members 20 are manufactured separately and subsequently joined together with a suitable attachment means, such as by insert molding, ultrasonic welding, friction welding, or with the use of adhesives, such as glues, epoxies, or cements. According to this embodiment, the material of the flexible members 20 may comprise the same material as the body 12 or a different material.

Suitable materials for the body 12 of the dental wedge 10 and the flexible members 20 include, but are not limited to nylon, polyethylene, polypropylene, polystyrene, elastomers, thermoplastics, thermoset plastics, chemical set plastics and equivalents. The dental wedges of the invention can comprise any such suitable material or any combination thereof.

As shown in FIGS. 1 and 2, the flexible members 20 may be rounded at their ends 26. This embodiment is useful for minimizing the possibility of abrading the gingiva or other sensitive mouth tissues with the flexible members 20 while inserting the dental wedge 10 between the teeth. It should be appreciated, however, the shape of the flexible members 20 shown in FIGS. 1 and 2 may be modified to accommodate different needs and preferences. Some alternative embodiments of the flexible members 20 and dental wedges 10 of the invention are illustrated in FIGS. 3–9, as described below.

Figure 3:
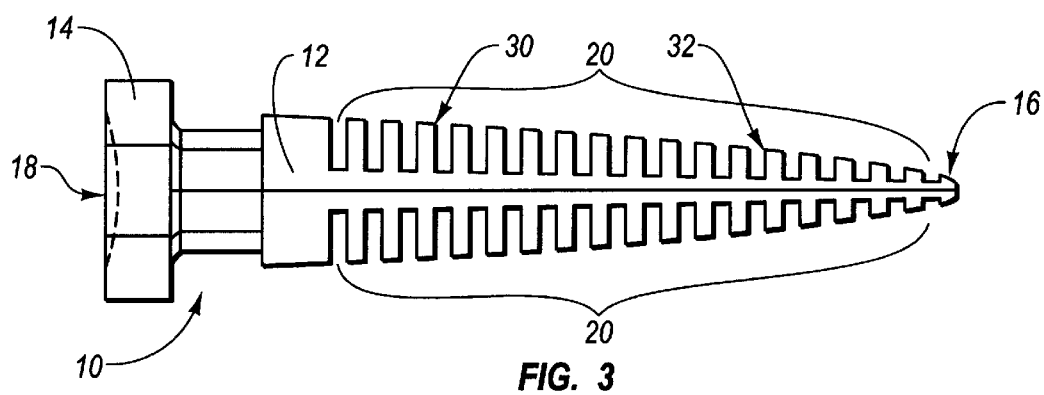
FIG. 3 is a top view of one embodiment of the dental wedge of the invention that includes a body and multiple flexible members with rectilinear shapes protruding away from the body.

In one alternative embodiment, shown in FIG. 3, the flexible members 20 are substantially rectilinear, or at least have a substantially rectilinear foot print when the dental wedge 10 is viewed from the top or bottom. This embodiment is useful for providing edges, such as front edge 30 and back edge 32, for enhancing the retention capabilities of the dental wedge 10 of the invention. According to this embodiment, each of the flexible members 20 is provided with a corresponding front edge 30 and back edge 32. When the dental wedge 10 is initially forced between two adjacent teeth then at least some of the flexible members 20 will be forced to bend backwards, towards the proximal end 14, causing their front edges 30 to press against the surfaces of the teeth. The front edges 30 are then able to slip into the contours of the teeth and are able to cling onto any irregularities, thereby providing increased frictional forces for the dental wedge 10 to resist slipping out from between the teeth.

It should be appreciated that the back edges 32 of the flexible members 20 are also useful for helping retain the dental wedge 10 in place between adjacent teeth. In particular, once the dental wedge 10 is inserted between the teeth, some of the flexible members 20 near the distal end 16 will pass completely through and beyond the narrow regions between the teeth. These flexible members 20 will no longer be forced to bend against the body 12 of the dental wedge 10 and will spring back into their original positions. When the dental wedge 10 is pulled back out from between the teeth, the flexible members 20 that have passed completely through the narrow passages of the teeth will be forced to bend in the opposite direction, towards the tip or distal end 16 of the dental wedge 10, thereby forcing the back edges 32 of the flexible members 20 against the surfaces of the teeth. The back edges 32 of the flexible members 20 are then able to catch against any irregularities and contours of the teeth. It will be appreciated that this generally increases the frictional forces of the flexible members 20 for resisting removal of the dental wedge 10 from between the teeth.

Figure 4:
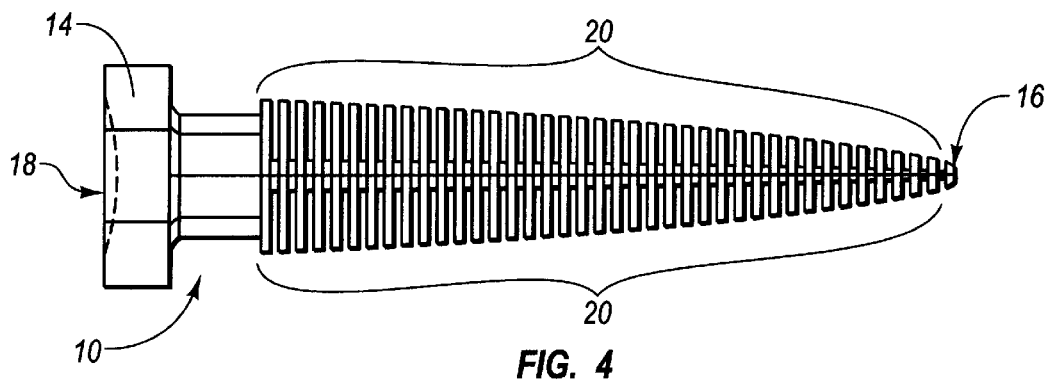
FIG. 4 is a top view of one embodiment of the dental wedge of the invention that includes a body and multiple flexible members that are very thin protruding away from the body.

In another embodiment, shown in FIG. 4, the flexible members 20 are extremely thin. This thin design increases the flexibility of the flexible members 20, which further provides the dental wedge 10 with increased retention capabilities. In particular, the increased flexibility of the flexible members 20 enables the flexible members to conformingly bend and compress against the surfaces of the teeth between which the dental wedge 10 is inserted. As the flexible members 20 conform to the surfaces of the teeth, the contact surface area over which friction is applied between the flexible members 20 and the surfaces of the teeth is increased, thereby increasing the retention capabilities of the dental wedge 10.

Accordingly, the embodiment shown in FIG. 4 is particularly useful when the flexible members 20 are composed of materials that are semi-rigid because the thin design allows the flexible members 20 to bend without requiring too much force to be applied by a practitioner who is inserting the dental wedge 10 between a patient's teeth. Minimizing the forces that are required to insert the dental wedge 10 between the teeth is desirable because of the potential risk of a tool slipping off of the dental wedge and injuring the patient.

Figure 5:
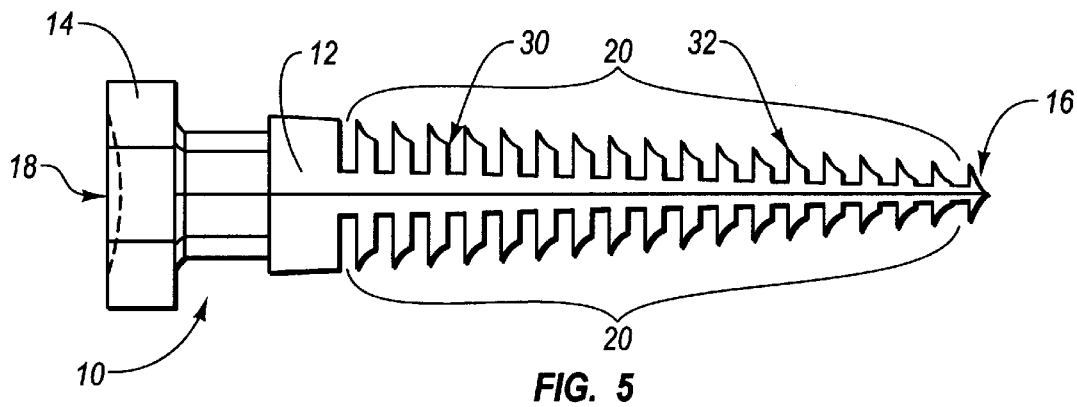
FIG. 5 is a top view of one embodiment of the dental wedge of the invention that includes a body and multiple flexible members with rectilinear shapes and angled ends protruding away from the body.

FIG. 5 illustrates another embodiment in which the flexible members 20 are modified so as to reduce the forces that are required to insert the dental wedge 10 between adjacent teeth. As shown, the flexible members 20 of FIG. 5 are similar to the rectilinear flexible members 20 of FIG. 3. However, in FIG. 5 the flexible members 20 are angled, with a retracted front edge 30 and a protracted back edge 32. According to this embodiment, the dental wedge 10 can be inserted between the teeth with minimal resistance because the front edge 30 is retracted and cannot therefore effectively catch hold against the surfaces of the teeth while the dental wedge 10 is being inserted. The back edge 32 of the flexible members 20, however, is extended and can catch hold against the irregularities of the teeth, thereby resisting removal of the dental wedge 10 and helping prevent the dental wedge 10 from unintentionally slipping out from between the teeth.

Figure 6:
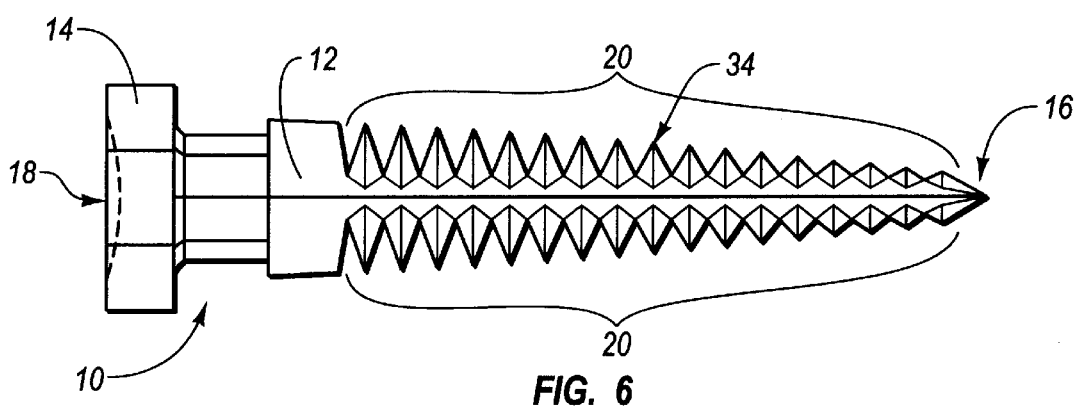
FIG. 6 is a top view of one embodiment of the dental wedge of the invention that includes a body and multiple flexible members with triangular shapes protruding away from the body.
Figure 7:
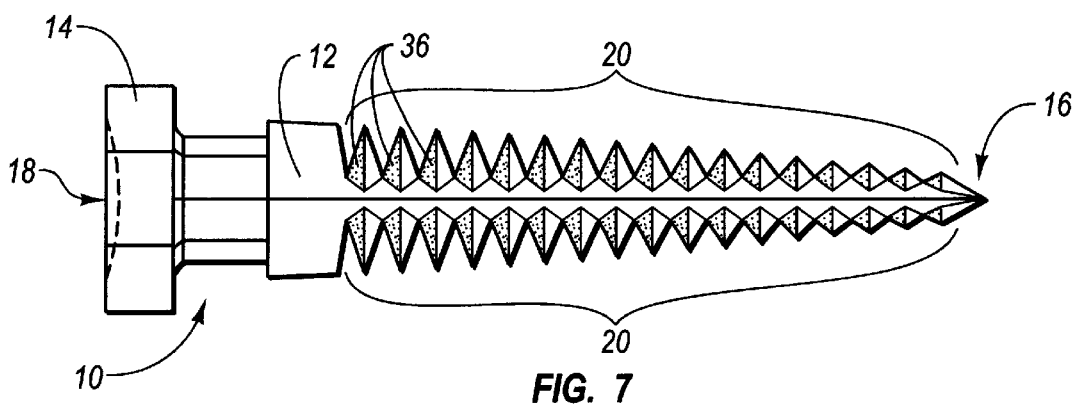
FIG. 7 is a top view of one embodiment of the dental wedge of the invention that includes a body and multiple flexible members with triangular shapes and textured surfaces protruding away from the body.

FIG. 6 illustrates yet another embodiment of the dental wedge 10 of the invention. In this embodiment, the flexible members 20 have a triangular shape and only a single edge 34 for enhancing the retention capabilities of the dental wedge 10. This embodiment is useful when the flexible members 20 are composed of materials that are somewhat compressible and elastomeric. The present invention contemplates the use of materials that are completely resilient, i.e., materials that will completely spring back into their original shape after being deformed, as well as materials that are not entirely resilient but which exhibit some degree of semi-set or deformation memory. The less resilient materials allow the flexible members 20 to substantially increase the level of spreading force between the teeth while still being able to rebound enough to conform to the irregularities of, and between, the teeth.

By conforming to the shape of the teeth, the flexible members 20 are able to increase the surface area over which friction is applied between the dental wedge 10 and the teeth. The increased frictional surface area helps hold the dental wedge 10 in place and keep the dental wedge from slipping out from between the teeth. To further enhance the retention capabilities of the dental wedges 10 of the invention, the flexible members 20 may also comprise a textured surface. For example, in FIG. 7 the backsides 36 of the flexible members 20 are textured with a gritty surface.

The gritty surface on the backsides 36 of the flexible members 20 enhances the retention capabilities of the dental wedge 10 by increasing the frictional coefficient applied by the flexible members 20 when the dental wedge 10 is removed from between the teeth. The front of the flexible members 20 is left smooth and untextured so as to minimize the frictional coefficient and forces involved when the dental wedge 10 is inserted between the teeth. It will be appreciated that any dental wedge of the invention may be textured so as to provide the benefits that have been described in reference to dental wedge 10 of FIG. 7.

Figure 8:
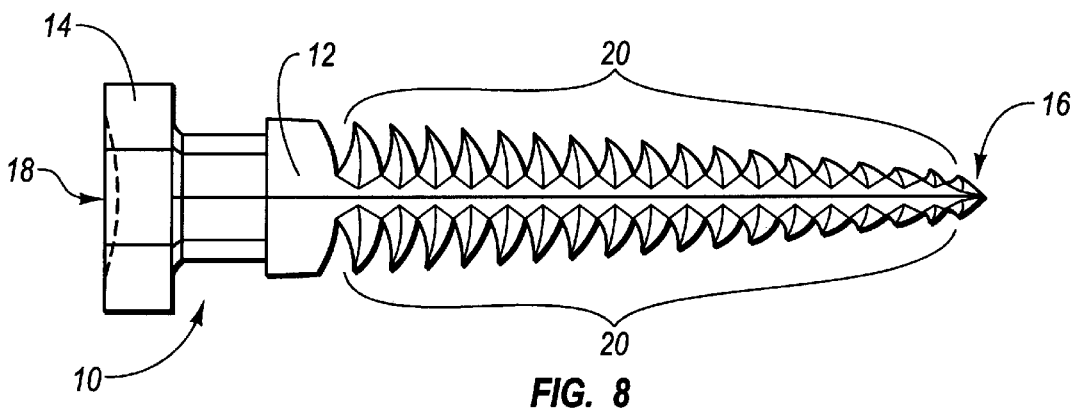
FIG. 8 is a top view of one embodiment of the dental wedge of the invention that includes a body and multiple flexible members that are curved and pointed protruding away from the body.

The flexible members 20 may also be curved. According to one embodiment, as shown in FIG. 8, the flexible members 20 are curved towards the proximal end 14. This embodiment is particularly useful for minimizing the resistance of the flexible members 20 when they are forced to bend towards the proximal end 14, such as when the dental wedge 10 is inserted between the teeth, while at the same time increasing the resistance of the flexible members 20 when they are forced to bend towards the distal end 16, such as when the dental wedge 10 is removed from between the teeth. This will be shown and described in more detail below in reference to FIGS. 9 and 10.

According to another embodiment of the invention, which is not shown, the flexible members 20 may be coated with an elastomeric material. The elastomeric material can enhance the ability of the flexible members 20 to spring back into place after being bent out of shape. The elastomeric material can also protect sensitive mouth tissue from sharp edges of the flexible members 20. As described above, the flexible members 20 themselves may also comprise elastomeric materials. Suitable elastomeric materials include, but are not limited to rubber, silicone, latex, elastic, chemical set and thermoset plastics. Additional benefits of using elastomeric material, as well as other embodiments of dental wedges incorporating elastomeric sides are further disclosed in U.S. patent application Ser. No. 09/897,563, entitled "Dental Wedge With Elastomeric Sides For Enhanced Retention," filed Jul. 2, 2001, which is hereby incorporated by reference.

Figure 9:
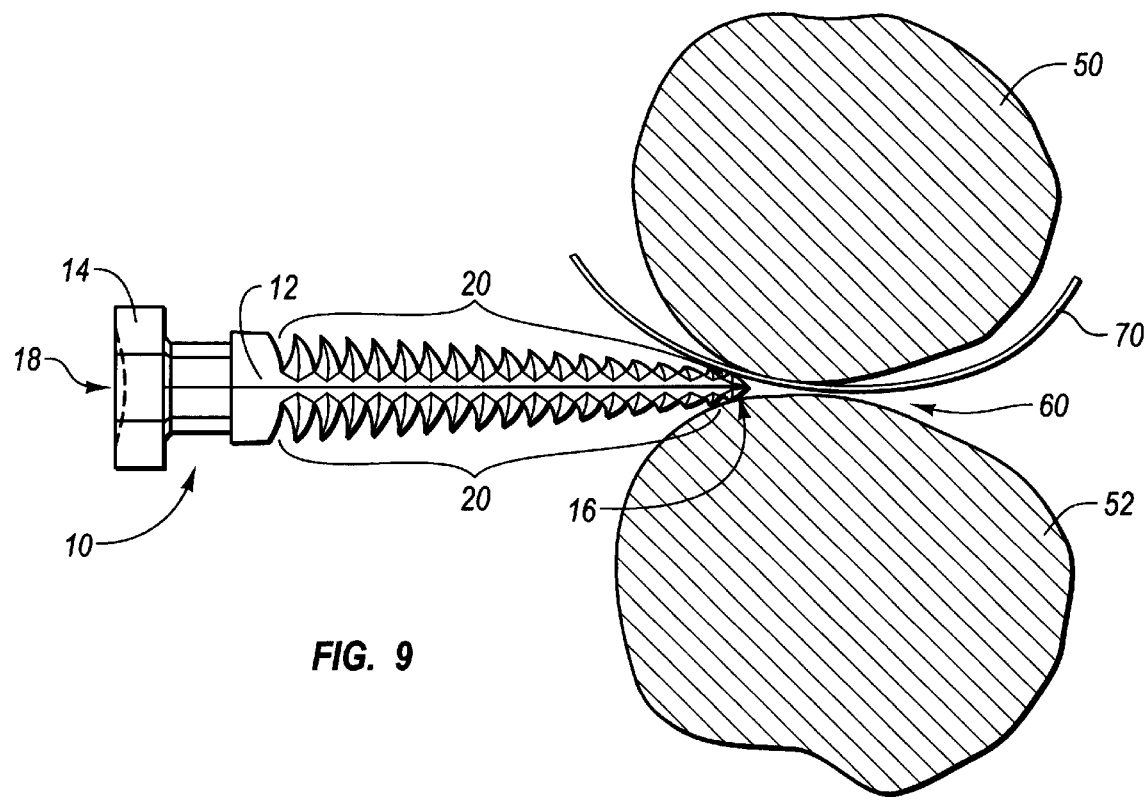
FIG. 9 is a top view of two adjacent teeth with a matrix band disposed between the teeth and a dental wedge of the invention positioned to be inserted between the teeth, with the tip of the dental wedge placed proximate the interproximal space between the two adjacent teeth.
Figure 10:
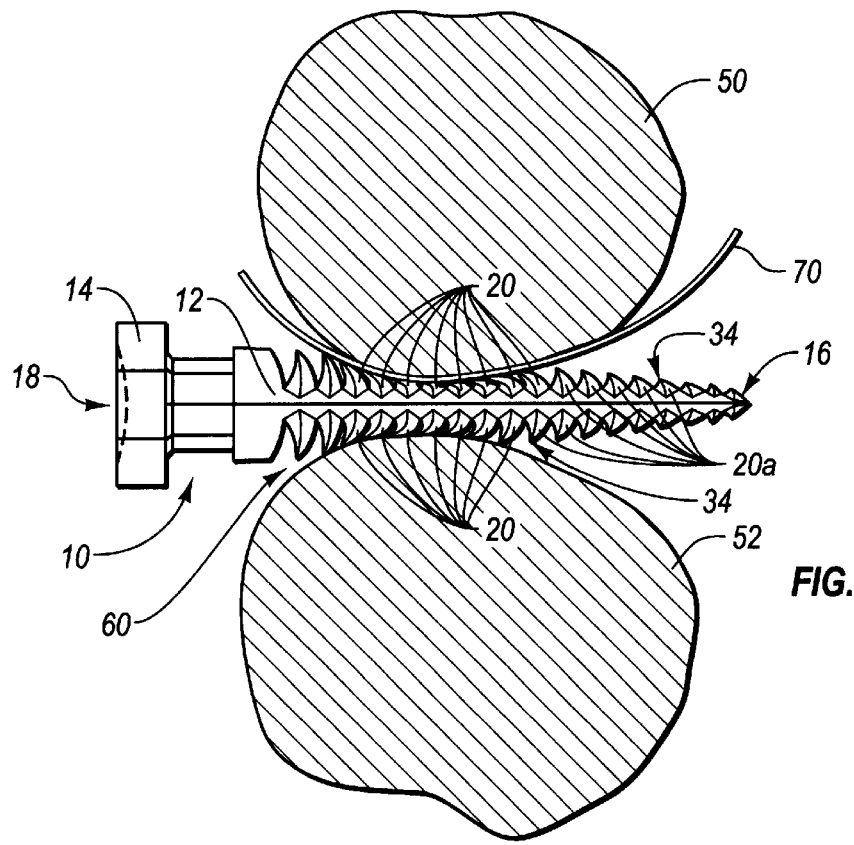
FIG. 10 is a top view of two teeth with a matrix band and a dental wedge of the invention inserted completely between the two teeth, such that some of the flexible members are bent between the body of the dental wedge and the matrix band, urging the matrix band conformingly against the surface of the tooth against which it is disposed, and with other of the flexible members bent between the body of the dental wedge and the tooth opposite the matrix band.

A preferred method for using the dental wedge of the present invention to separate teeth and to hold matrix bands in place will now be shown and described in reference to FIGS. 9 and 10.

FIG. 9 is a top cross-sectional view of two adjacent teeth 50 and 52. FIG. 9 also shows dental wedge 10 in position to be inserted between teeth 50 and 52, with the distal end 16 or tip inserted slightly within the interproximal space 60 between the teeth 50 and 52. To further separate teeth 50 and 52, the tip 16 is pushed into and through the interproximal space 60 between the teeth 50 and 52 by applying a force to the back of dental wedge 10 at the proximal end 14. The force can be applied by pushing directly on the face 18 or by gripping and pushing the head of the proximal end 14 with cotton pliers or another device, as described above in reference to FIG. 1. Once an adequate force is applied to proximal end 14, dental wedge 10 will be forced between the teeth 50 and 52, causing the teeth 50 and 52 to separate.

FIG. 9 also depicts a matrix band 70 that is positioned against tooth 50. It will be appreciated that when the dental wedge 10 is inserted between the teeth, the flexible members 20 will force the matrix band 70 against tooth 50 and will securely hold it in place. Matrix band 70 may comprise any matrix band that is commonly used in the industry for providing form during obturation. In practice, it is essential that a matrix band be securely held in place against a tooth receiving a filling, otherwise the filling may flow beyond the form of the matrix band and create ridges and irregular surfaces that will have to be filed down or that may lead to further dental complications, such as misalignment of teeth, capture of food particles, infection, etc. Accordingly, it will be appreciated that the dental wedges of the present invention are at least beneficial for minimizing these problems by providing flexible members 20 with increased retention capabilities for enabling the dental wedges 10 of the invention to remain in place and to securely hold the matrix band 70 in placement against the tooth 50, as desired.

FIG. 10 shows that once dental wedge 10 is forced within the interproximal space 60 between the teeth 50 and 52, some of the flexible members 20 are forced to bend and compress. By bending and compressing, the flexible members 20 are able to conform to the surfaces of tooth 52 and matrix band 70, thereby increasing the surface area over which dental wedge 10 is in contact with tooth 52 and matrix band 70. It will be appreciated that this directly improves the retention capabilities of dental wedge 10 because friction is applied over the entire area in which dental wedge 10 makes contact with the surfaces of tooth 52 and matrix band 70. It should also be appreciated that the edges of the bent flexible members also increase the retention capabilities of the dental wedge 10 because the edges are able to catch against irregularities and contours of the tooth 52, thereby preventing dental wedge 10 from slipping out from between the teeth 50 and 52.

Also shown in FIG. 10, some of the flexible members 20a have passed completely through the narrow regions between the teeth, such that they are no longer bent or compressed. These flexible members 20a, having sprung back to their original shape, are further able to resist the unintentional slipping of the dental wedge 10 out from between the teeth 50 and 52. In particular, the edges of the flexible members 20a can catch onto irregularities of the surfaces of tooth 52, thereby creating increased frictional forces for holding the dental wedge 10 in place. The flexible members 20a will also be forced to bend or compress backwards, towards the tip or distal end 16 of the dental wedge 10 as the dental wedge 10 is pulled back out from between the teeth 50 and 52, which as generally described above in reference to FIG. 8, further enhances retention capabilities of the dental wedges 10 of the present invention over the existing dental wedges of the prior art.

As shown in FIG. 10, the flexible members 20 of the dental wedge 10 of the invention are also useful for pressing and holding a matrix band 70 conformingly in place against a tooth 50. In particular, the flexible members 20 and 20a of the dental wedge 10 bias against the matrix band 70 at multiple discrete locations, thereby urging the matrix band 70 to conform to the shape of the tooth 50 against which the matrix band 70 is disposed.

The benefits and advantages of the present invention extend to these and other applications by providing flexible members that generally enable the dental wedges to maintain a desired position between teeth, while conforming to the shape of the teeth, so as to effectively separate the teeth and/or for holding matrix bands or other similar devices firmly in place against the surfaces of the teeth.

The invention, as it has been described herein, generally provides a dental wedge with serrated sides or flexible members that protrude away from the sides of the dental wedge. When the dental wedge is inserted between teeth, it causes the teeth to separate and the flexible members to bend conformingly to the surfaces of the separated teeth, thereby providing increased frictional forces and retention capabilities for remaining in position between the teeth. The flexible members may also comprise edges and textured surfaces for further enhancing the retention capabilities of the dental wedges of the invention. It should be appreciated that these benefits of the invention are advantages over the prior art.

It should also be appreciated that the present invention may be embodied in other forms without departing from its spirit or essential characteristics. For example, the shape of the body of the dental wedge and the flexible members affixed to the dental wedge may vary. The flexible members may also be disposed on only a single side of the dental wedge or over any portion of the dental wedge. Furthermore, the flexible members may be covered with other materials. Accordingly, the invention is not limited to dental wedges comprising only flexible members.

As properly understood, the preceding description of specific embodiments is illustrative only and in no way restrictive. The scope of the invention is, therefore, indicated by the appended claims as follows.

What is claimed and desired to be secured by United States Letters Patent is:

1. A dental wedge for insertion between adjacent teeth, comprising:
    a rigid body configured to be inserted within an interproximal space between two adjacent teeth, wherein the rigid body tapers from a proximal end to a distal end; and
    a plurality of flexible members protruding away from the rigid body, the plurality of flexible members being configured to bend towards at least one of the proximal end and the distal end of the rigid body.

2. A dental wedge as defined in claim 1, wherein at least one of the flexible members comprises a substantially rectilinear shape.

3. A dental wedge as defined in claim 1, wherein at least one of the flexible members comprises an end that is rounded.

4. A dental wedge as defined in claim 1, wherein at least one of the flexible members comprises an end with edges.

5. A dental wedge as defined in claim 1, wherein at least one of the flexible members comprises a substantially triangular shape.

6. A dental wedge as defined in claim 5, wherein at least one of the flexible members comprises at least one gritty surface, said at least one gritty surface substantially facing the proximal end.

7. A dental wedge as defined in claim 1, wherein at least one of the flexible members is curved towards the proximal end.

8. A dental wedge as defined in claim 1, wherein at least one of the flexible members is composed of at least one of nylon, polycarbonate, polystyrene, polyethylene, and polypropylene.

9. A dental wedge as defined in claim 1, wherein the rigid body is composed of the same material as at least one of the flexible members.

10. A dental wedge as defined in claim 1, wherein said rigid body further comprises:
    a substantially triangular cross-sectional area; and
    a base,
    wherein at least one of the flexible members protrudes away from the first and second sides near the base.

11. A dental wedge as defined in claim 1, further comprising a layer of elastomeric material, wherein said layer of elastomeric material is layered over at least one of the flexible members.

12. A dental wedge as defined in claim 1, further comprising a head having a gritty surface.

13. A dental wedge as defined in claim 12, wherein said head further comprises at least one of an octagonal shape and a concaved surface.

14. A dental wedge as defined in claim 1, wherein at least one of the flexible members comprises at least one edge, and wherein said at least one edge is configured to hold the dental wedge in place within the interproximal space between two adjacent teeth.

15. A dental wedge as defined in claim 1, wherein at least one of the flexible members comprises two edges.

16. A dental wedge as defined in claim 1, wherein at least some of the flexible members are configured to bend, such that when said dental wedge is inserted within the interproximal space between two adjacent teeth, the at least some of the multiple flexible members are bent between the rigid wedge shaped body of the dental wedge and at least one of the two adjacent teeth.

17. A dental wedge for insertion between adjacent teeth, comprising:
- a rigid and tapered body that is configured for separating two adjacent teeth upon being inserted between the adjacent teeth; and
- a plurality of flexible members protruding away from the rigid body, wherein at least some of the flexible members are configured to temporarily bend between the rigid body and at least one of the adjacent teeth when the dental wedge is inserted between the adjacent teeth.

18. A dental wedge as defined in claim 17, wherein at least one of the flexible members is configured to bend towards at least one of the proximal end and the distal end when the dental wedge is inserted within the interproximal space between two adjacent teeth.

19. A dental wedge as defined in claim 17, wherein at least one of the flexible members comprises a gritty surface.

20. A dental wedge as defined in claim 17, wherein at least one of the flexible members comprises at least one edge, the at least one edge being configured to hold the dental wedge in place within the interproximal space between two adjacent teeth.

* * * * *

UNITED STATES PATENT AND TRADEMARK OFFICE
CERTIFICATE OF CORRECTION

PATENT NO. : 6,468,080 B1
DATED : October 22, 2002
INVENTOR(S) : Dan E. Fischer and Bruce S. McLean It is certified that error appears in the above-identified patent and that said Letters Patent is hereby corrected as shown below:

Column 2,
Line 2, after "contact" delete "-"
Line 9, after "problems" replace "associates" with -- associated --

Column 10,
Line 62, after "bend" delete ", such"
Line 63, before "when" delete "that"
Lines 64-67, after "teeth" delete ", the at least some of the multiple flexible members are bent between the rigid wedge shaped body of the dental wedge and at least one of the two adjacent teeth"

Signed and Sealed this

First Day of April, 2003

JAMES E. ROGAN
*Director of the United States Patent and Trademark Office*